United States Patent
Dogo-Isonagie et al.

(10) Patent No.: US 11,166,890 B2
(45) Date of Patent: Nov. 9, 2021

(54) PEROXYMONOSULFATE TOOTHPOWDER COMPOSITION FOR TENACIOUS STAINS

(71) Applicant: Colgate-Palmolive Company, New York, NY (US)

(72) Inventors: Cajetan Dogo-Isonagie, Highland Park, NJ (US); Lin Fei, Kendall Park, NJ (US); Suman Chopra, Monroe, NJ (US); Jennifer Gronlund, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/324,764

(22) PCT Filed: Aug. 11, 2016

(86) PCT No.: PCT/US2016/046543
§ 371 (c)(1),
(2) Date: Feb. 11, 2019

(87) PCT Pub. No.: WO2018/031018
PCT Pub. Date: Feb. 15, 2018

(65) Prior Publication Data
US 2019/0167545 A1   Jun. 6, 2019

(51) Int. Cl.
*A61K 8/23* (2006.01)
*A61Q 11/00* (2006.01)
*A61K 8/02* (2006.01)
*A61K 8/22* (2006.01)

(52) U.S. Cl.
CPC ............ *A61K 8/23* (2013.01); *A61K 8/022* (2013.01); *A61K 8/22* (2013.01); *A61Q 11/00* (2013.01)

(58) Field of Classification Search
None
See application file for complete search history.

(56) References Cited

U.S. PATENT DOCUMENTS

| | | | | |
|---|---|---|---|---|
| 4,115,293 A | * | 9/1978 | Schoenholz | A61K 8/02 252/188.1 |
| 4,612,191 A | | 9/1986 | Yeh et al. | |
| 4,886,669 A | | 12/1989 | Ventouras | |
| 6,106,861 A | | 8/2000 | Chauveau et al. | |
| 6,264,703 B1 | | 7/2001 | Coope | |
| 6,274,122 B1 | * | 8/2001 | McLaughlin | A61C 19/063 128/860 |
| 6,596,311 B1 | | 7/2003 | Dobetti | |
| 6,743,443 B1 | | 6/2004 | Furitsu et al. | |
| 6,811,793 B2 | | 11/2004 | Wehling | |
| 7,501,409 B2 | | 3/2009 | Murakami et al. | |
| 7,815,897 B1 | | 10/2010 | Wehiing et al. | |
| 8,211,407 B2 | * | 7/2012 | Deckner | A61K 8/25 424/49 |
| 8,377,995 B2 | | 2/2013 | Ikeda et al. | |
| 9,789,048 B2 | | 10/2017 | Prencipe | |
| 2005/0169986 A1 | | 8/2005 | Tian et al. | |
| 2007/0071695 A1 | * | 3/2007 | Chopra | A61K 8/20 424/53 |

FOREIGN PATENT DOCUMENTS

| | | | | |
|---|---|---|---|---|
| BE | 1020399 A5 | * | 9/2013 | |
| BE | 1020399-A5 MT | * | 9/2013 | |
| EP | 0157464 | | 10/1987 | |
| JP | H07109212 B2 | * | 11/1995 | ............ F16B 37/14 |
| WO | WO-0009079 A1 | * | 2/2000 | ............ A61K 8/22 |
| WO | 2009/133525 | | 11/2009 | |
| WO | 2016/064882 | | 4/2016 | |

OTHER PUBLICATIONS

International Search Report and Written Opinion of the International Searching Authority in International Application No. PCT/US2016/046543, dated Nov. 25, 2016.

* cited by examiner

*Primary Examiner* — Celeste A Roney

(57) ABSTRACT

A solid oral care composition, e.g., a tablet or powder, comprising an alkali metal peroxymonosulfate as an effective bleaching agent for the bleaching of tenacious tooth stains, such as tobacco stains and coffee stains.

17 Claims, No Drawings

PEROXYMONOSULFATE TOOTHPOWDER COMPOSITION FOR TENACIOUS STAINS

BACKGROUND

Products that are presently available to whiten teeth include a variety of different ingredients, and the primary active ingredient is often a peroxide source such as hydrogen peroxide. The use of peroxide agents can present difficulties in both formulation and long term stability of the resulting compositions. Thus, alternative bleaching agents with improved stability and tolerability are desired.

A particularly challenging use of existing tooth whitening agents is in the removal of tobacco stains. Tobacco tooth stains result from the nicotine and tar found in tobacco products, including cigarette and cigar smoke and chewing tobacco. While nicotine is itself not strongly colored, oxidation by air creates strong yellow to brown stains which are difficult to remove. When tobacco is inhaled or placed in the mouth, nicotine and tar settle into the oral cavity. These chemicals leach into the microscopic openings in tooth enamel, resulting over time in severe yellow/brown discoloration of the tooth surfaces as these chemicals oxidize. Coffee stains and stains caused by chewing paan are similarly problematic. Existing tooth whitening compositions have difficulty bleaching these types of tenacious stains.

Peroxysulfuric acid, and its salts, the peroxysulfates, are powerful oxidizing and stain removing agents. They are currently used for various consumer purposes, including denture cleaning. The most common peroxymonosulfate oxidizing agent is potassium peroxymonosulfate, commonly referred to as MPS.

Potassium monoperoxysulfate has seen limited use in dental whitening compositions because of its instability in aqueous solution, especially in aqueous solution near or above neutral pH. In fact, potassium monoperoxysulfate has been known to degrade even in the presence of small quantities of water and heat. Formulation of potassium monoperoxysulfate as the triple salt mixture of potassium peroxymonosulfate, potassium hydrogen sulfate and potassium sulfate ($2KHSO_5 \cdot KHSO_4 \cdot K_2SO_4$) enhances the stability of the oxidizing agent. Nevertheless, there is still a need for improved formulations of MPS for stable oral care products for the treatment of tenacious tooth stains, such as tobacco and coffee stains.

BRIEF SUMMARY

The present disclosure provides a solid oral care composition, e.g., a tablet or powder, comprising an alkali metal peroxymonosulfate as an effective oxidizing agent for the bleaching of tenacious tooth stains. In some embodiments, the peroxymonosulfate salt is sodium or potassium peroxymonosulfate. In some embodiments, the peroxymonosulfate salt is potassium peroxymonosulfate, optionally present as the triple salt mixture of potassium peroxymonosulfate, potassium hydrogen sulfate and potassium sulfate ($2KHSO_5 \cdot KHSO_4 \cdot K_2SO_4$). In some embodiments, the composition is combined with water or an aqueous solution (e.g., an oral care solution) for use by the consumer to bleach tenacious stains. Once the toothpowder is dissolved or suspended in water or an aqueous solution, the consumer can use the resulting liquid as a typical toothpaste. The present disclosure provides compositions as well as methods of use.

Further areas of applicability of the present disclosure will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Open terms such as "include," "including," "contain," "containing" and the like mean "comprising." In this description, unless otherwise stated, the use of the singular also includes the plural. For example, "a lubricant" also comprehends the case where more than one lubricant is used In one aspect, the present disclosure provides a solid oral care composition, e.g., a tooth powder, for the diminution and/or removal of tenacious tooth stains. Such tenacious stains include those caused by exposure to tobacco smoke, chewing tobacco, paan and coffee.

The solid composition of the present disclosure comprises a tooth-whitening effective amount of an alkali metal peroxymonosulfate salt. Specific examples of such salts are sodium peroxymonosulfate, potassium peroxymonosulfate, and lithium peroxymonosulfate. In some embodiments, the solid composition of the present disclosure is a toothpowder.

In one embodiment, the peroxymonosulfate is potassium peroxymonosulfate (also known as potassium monopersulfate or MPS). The potassium peroxymonosulfate may be present as the triple salt mixture of potassium peroxymonosulfate, potassium hydrogen sulfate and potassium sulfate ($2KHSO_5 \cdot KHSO_4 \cdot K_2SO_4$). This triple salt is sold commercially as both Oxone® and Caroat®. Caroat®, for example, is approximately 47 wt % potassium peroxymonosulfate ($KHSO_5$).

In one embodiment, the compositions of the present disclosure are effective to result in improved tooth whitening when used twice daily in a mouthrinse or toothpaste for about three months as compared to a control mouthrinse or toothpaste without the peroxymonosulfate salt.

Peroxymonosulfate salts have limited stability in aqueous solutions and are therefore best stored as dry (e.g., anhydrous) powders. Preferably, the solid composition, e.g., tablet, granules or powder, is individually packaged and sealed into unit dose packages. In some embodiments, the solid composition may be stored in an air tight, moisture-proof package, e.g., sachets, sealed metal foil pouches, blister packs, and desiccant capped tubes or the like.

The solid compositions of the present disclosure may have a low water content (e.g., substantially anhydrous or anhydrous). As used herein, the terms "low water content," "water content" and "water" refer to the total concentration of water, including any free water and all water contained in any ingredients. In various embodiments of the composition, the amount of water is an amount of less than 4% by weight, or less than 3% by weight, or less than 2% by weight, or less than 1% by weight, or less than 0.5% by weight, or less than 0.1%. For example, the minimum amount of water may be about 0.0001%, such as a range of 0.0001% to 4% by weight, or 0.0001% to 0.5% by weight or 0.0001% to 0.1% by weight.

The solid composition of the present disclosure can be in a variety of forms including, e.g., powder (e.g., a free flowing granulation), tablet, caplet (type of tablet), granule, pellet, wafer, film and bead.

The amount of peroxymonosulfate salt, e.g., sodium or potassium peroxymonosulfate, in the solid compositions of the invention is effective to result in the diminution or removal of tenacious tooth stains, especially tobacco stains and/or coffee stains. The amount of peroxymonosulfate salt typically is about 0.1% to about 50%, such as in one embodiment about 0.75% to about 40%, in another embodiment about 1% to about 20%, in another embodiment about 1% to about 10%, by weight of the total composition. In particular embodiments, the composition may comprise 0.5% to 10%, 1 to 10%, 2 to 8%, 4 to 6% or about 5%, by weight, of peroxymonosulfate salt. As used herein, in reference to triple salt mixtures, this amount refers only to the amount of peroxymonosulfate salt (i.e., $HSO_5$ salt, such as $NaHSO_5$ or $KHSO_5$).

The compositions of the present disclosure may optionally include one or more drying agents, for example, hygroscopic drying agents. Examples of drying agents include, but are not limited to, phosphates, pyrophosphates and other polyphosphates, calcium lactate, calcium lactophosphate, double salts of calcium lactate; and mixtures thereof. Other drying agents include silica gels and precipitates; aluminas; and mixtures thereof. Specific examples include, but are not limited to, dicalcium orthophosphate dihydrate, calcium pyrophosphate, tricalcium phosphate, calcium polymetaphosphate, insoluble sodium polymetaphosphate, potassium metaphosphate, tricalcium phosphate, trimagnesium phosphate, and magnesium orthophosphate, hydrated alumina, aluminum silicate, zirconium silicates, bentonite, sodium sulfate, magnesium sulfate, calcium sulfate, beta calcium pyrophosphate, or calcium carbonate. Pyrophosphate salts may also be used in the present invention as anticalculus agents or as buffering agents. Pyrophosphate salts suitable for the present compositions include dialkali metal pyrophosphate salts, tetra alkali metal pyrophosphate salts, and mixtures thereof. Disodium dihydrogen pyrophosphate, tetrasodium pyrophosphate, and tetrapotassium pyrophosphate in their unhydrated as well as hydrated forms are the preferred species. In various embodiments, the drying agents are present in an amount of about 0.1% to about 60%, about 1% to about 30%, about 1% to about 10%, or about 1% to about 5% by weight of the total composition, or about 2%, about 3%, about 4% or about 5%.

In some embodiments, the compositions of the present disclosure contain an abrasive. Examples of abrasives include, but are not limited to, calcium carbonate (precipitated or natural), sodium carbonate, sodium chloride, sodium bicarbonate, silica, arginine bicarbonate, calcium phosphate, calcium pyrophosphate, dicalcium phosphate, zinc oxide, calcined alumina, or combinations thereof. In some embodiments the abrasive is calcium carbonate, such as either natural calcium carbonate, precipitated calcium carbonate, or a combination thereof. The composition may comprise one or more abrasives in an amount of 10-90% by weight of the composition, e.g., 30-90%, or 50-90%, or 60-90%, or 70-90%, or 80-90% or 85-90%, or about 86%.

In some embodiments, the compositions of the present disclosure contain a buffering agent. Examples of buffering agents include anhydrous carbonates such as sodium carbonate, sesquicarbonates, bicarbonates such as sodium bicarbonate, silicates, bisulfates, phosphates such as monopotassium phosphate and dipotassium phosphate, citrates, pyrophosphates (sodium and potassium salts) and combinations thereof. The amount of buffering agent is sufficient to provide a pH of about 5 to about 9, preferable about 6 to about 8, and more preferable about 7, when the composition is dissolved in water, a mouthrinse base, or a toothpaste base. Typical amounts of buffering agent are about 5% to about 35%, in one embodiment about 10% to about 30%, in another embodiment about 15% to about 25%, by weight of the total composition.

In some embodiments, the solid compositions of the invention contain a disintegrating agent. Disintegrating agents include natural starches, such as maize starch, potato starch etc., directly compressible starches such as starch 1500, modified starches such as carboxymethyl starches and sodium starch glycolate which are available as PRIMOJEL® and EXPLOTAB® and EXPLOSOL® and starch derivatives such as amylose. Other examples are cross-linked polyvinylpyrrolidones, e.g. crospovidones available as e.g. POLYPLASDONE XL® and KOLLIDON XL®; modified celluloses such as cross-linked sodium carboxymethylcelluloses available as, e.g., AC-DI-SOL®, PRIMELLOSE®, PHARMACEL XL®, EXPLOCEL®, and NYMCEL ZSX®; alginic acid and sodium alginate; microcrystalline cellulose, e.g. AVICEL®, PHARMACEL®, EMCOCELL®, VIVAPUR®; and methacrylic acid-divinylbenzene copolymer salts available as e.g., AMBERLITE® IRP-88. Other examples of the disintegrating agent are light silicic anhydride, calcium silicate, magnesium metasilicate aluminate, and carboxymethyl cellulose. In the present invention, each of them may be used solely or two or more thereof may be used jointly. Typical amounts of disintegrating agent are about 0.5% to about 20%, in one embodiment about 1% to about 5%, in another embodiment about 1% to about 3%, by weight of the total composition.

The compositions of the present disclosure optionally contain a binder, preferably a polymeric binder, which is compatible with an oxidizing agent, which adds bulk to the compositions and assists in holding the components of the composition together when in the form of a tablet. Examples of suitable polymeric binders include, e.g., starches, natural gums, (e.g., xanthan gum), cellulose gums, microcrystalline cellulose, maltodextrins, methylcellulose, cellulose ethers, sodium carboxymethylcellulose, ethylcellulose, gelatin, polyethylene glycol, polyvinylpyrrolidone, pectins, alginates, polyacrylamides, polyvinyloxozolidone, polyvinyl alcohols and mixtures thereof. The binder can also comprise one or more non-polymeric binders such as dextrose, lactose, sucrose, sorbitol, mannitol, xylitol and the like. Typically, the binder is present in the composition in an amount of about 10% by weight to about 60% by weight, about 15% by weight to about 50% by weight, or about 25% by weight to about 40% by weight.

The solid composition of the present disclosure is optionally an effervescent composition. The term "effervescent composition" as used herein means a composition that evolves gas bubbles when contacted with water or an aqueous solution. When the solid composition of the invention is an effervescent composition, it comprises an effervescent agent. The effervescent agent preferably is an effervescent couple that includes an acid and a base. The effervescent couple is activated when contacted with water, e.g., when the composition, e.g., powder, granule, or tablet, is placed in a glass of water. The water liberates the acid and base and enables the acid and base to react with each other to produce carbon dioxide gas, which imparts carbonation to the aqueous composition.

Examples of useful acids for an effervescent composition include citric acid, ascorbic acid, malic acid, adipic acid, tartaric acid, fumaric, succinic acid, sodium acid pyrophosphate, lactic acid, hexamic acid, and acid salts and acid anhydrides thereof, and mixtures thereof. Examples of useful acid anhydrides include citraconic anhydride, glucono-D-lactone, and succinic anhydride. Examples of useful acid salts include potassium bitartrate, acid citrate salts, sodium dihydrogen phosphate, disodium dihydrogen phosphate, sodium acid sulfite, and combinations thereof. When effervescent, the acid is present in the composition in an amount of about 10% by weight to about 60% by weight, about 15% by weight to about 50% by weight, or about 25% by weight to about 40% by weight.

The base for an effervescent composition preferably is capable of generating carbon dioxide. Examples of suitable carbonate bases include sodium bicarbonate, sodium carbonate, sodium sesquicarbonate, potassium carbonate, potassium bicarbonate, calcium carbonate, magnesium carbonate, magnesium oxide, sodium glycine carbonate, L-lysine carbonate, arginine carbonate, zinc carbonate, zinc oxide and mixtures thereof. When effervescent, the base is present in the composition in an amount of about 10% by weight to about 60% by weight, about 15% by weight to about 50% by weight, or about 25% by weight to about 40% by weight.

The compositions of the present disclosure optionally contain a lubricant. Various lubricants are suitable for use in the composition including water dispersible, water soluble, water insoluble lubricants and combinations thereof. Examples of useful water soluble lubricants include sodium benzoate, polyethylene glycol, L-leucine, adipic acid, and combinations thereof. The composition can also include water insoluble lubricants including, e.g., stearates (e.g., magnesium stearate, calcium stearate and zinc stearate), oils (e.g., mineral oil, hydrogenated and partially hydrogenated vegetable oils, and cotton seed oil) and combinations thereof. Other water insoluble lubricants include, e.g., animal fats, polyoxyethylene monostearate, talc, and combinations thereof. When the composition is in the form of a tablet, the composition preferably includes a sufficient amount of lubricant to enable the composition to be formed into tablets and released from a high speed tableting press in the form of a tablet. Typically, the amount of lubricant in the composition is about 1% by weight to about 15% by weight, about 1% by weight to about 12% by weight, about 2% by weight to about 10% by weight, or about 3% by weight to about 8% by weight. In one embodiment the composition includes sodium benzoate in an amount of about 1% by weight to about 3% by weight and polyethylene glycol in an amount of about 1% by weight to about 5.5% by weight.

The solid composition of the present disclosure can optionally contain whitening agents in addition to the peroxymonosulfate salt. Whitening agents are generally materials which are effective to provide whitening of a tooth surface to which it is applied, and include agents such as hydrogen peroxide and urea peroxide. In various embodiments, the compositions of the present disclosure may optionally comprise a peroxide whitening agent, comprising a peroxide compound. A peroxide compound is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In some embodiments, the peroxide compound comprises hydrogen peroxide. In some embodiments, the peroxide compound consists essentially of hydrogen peroxide. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite. One or more additional whitening agents are optionally present in a tooth-whitening effective total amount. In some embodiments the compositions additionally comprise an activator, e.g., tetraacetylethylenediamine.

The solid composition optionally can also include other ingredients, e.g., flavor agents; fillers; fluoride sources; surfactants; preservatives, e.g., sodium benzoate and potassium sorbate; color agents including, e.g., dyes and pigments; and sweeteners.

Examples of fluoride sources include sodium fluoride, sodium monofluorophosphate, zinc fluoride, stannous fluoride, amine fluorides, and the like. Fluoride sources are typically present in from 0.1 to 5% by weight of the composition, for example, from 0.1 to 2%, or 0.1 to 1%, or 0.5 to 1% or about 0.75%.

Examples of the surfactant that can be used are sodium lauryl sulfate, sorbitan fatty acid ester, polyoxyethylene (20) sorbitan monooleate (Polysorbate 80 or Tween 80), polyethylene glycol fatty acid ester, polyoxyethylene sorbitan fatty acid ester, polyoxyethylene alkyl ether, polyoxyethylene polyoxypropylene alkyl ether, polyoxyethylene polyoxypropylene block copolymer, polyoxyethylene alkyl phenyl ether, polyoxyethylene castor oil, polyoxyethylene hydrogenated castor oil, polyoxyethylene sorbitol fatty acid ester and polyoxyethylene glycerol fatty acid ester. In the present invention, each of them may be used solely or two or more thereof may be used jointly. Typical amounts of surfactant are 0.5% to 10%, in one embodiment 1% to 5%, in another embodiment 2% to 4%, or about 3%, by weight of the total composition.

Examples of the filler are crystalline cellulose, ethylcellulose, dextrin, various kinds of cyclodextrin (α-cyclodextrin, β-cyclodextrin and γ-cyclodextrin), sodium sulfate, as well as derivatives thereof and pullulan.

Useful flavor agents include natural and synthetic flavoring sources including, e.g., volatile oils, synthetic flavor oils, flavoring aromatics, oils, liquids, oleoresins and extracts derived from plants, leaves, flowers, fruits, stems and combinations thereof. Suitable flavor agents include, e.g., citric oils, e.g., lemon, orange, grape, lime and grapefruit, fruit essences including, e.g., apple, pear, peach, grape, strawberry, raspberry, cherry, plum, pineapple, apricot, and other fruit flavors. Other useful flavor agents include, e.g., aldehydes and esters (e.g., benzaldehyde (cherry, almond)), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), 2-dodedenal (citrus, mandarin) and mixtures thereof.

Suitable coloring agents include, e.g., food, drug and cosmetic (FD&C) colors including, e.g., dyes, lakes, and certain natural and derived colorants. Useful lakes include dyes absorbed on aluminum hydroxide and other suitable carriers.

Suitable sweetening agents include *stevia*, sugars such as sucrose, glucose, invert sugar, fructose, ribose, tagalose, sucralose, malitol, erythritol, xylitol, and mixtures thereof, saccharin and its various salts (e.g., sodium and calcium salt of saccharin), cyclamic acid and its various salts, dipeptide sweeteners (e.g., aspartame), acesulfame potassium, dihydrochalcone, glycyrrhizin, and sugar alcohols including, e.g., sorbitol, sorbitol syrup, mannitol and xylitol, and combinations thereof.

It is understood that while general attributes of each of the above categories of materials may differ, there may be some common attributes and any given material may serve multiple purposes within two or more of such categories of materials. All of the ingredients in the compositions may have functions in addition to their primary function, and may contribute to the overall properties of the composition, including its stability, efficacy, consistency, mouthfeel, taste, odor and so forth. For example, a binder may also function as a disintegrating agent and vice versa.

The solid compositions of the present disclosure can be made via techniques known in the art. Documents which disclose techniques which may be used to prepare the solid compositions of the present disclosure are U.S. Pat. Nos. 4,886,669; 6,106,861; 6,596,311; 6,743,443; 6,811,793; 7,501,409; 7,815,897; 8,377,995; and US patent application 2005/0169986, all of which are incorporated herein by reference in their entireties. In general, the ingredients and optional components can be kneaded with an organic solvent, filled in a mold and subjected to a compression-molding. The organic solvent can be an alcohol such as methanol, ethanol, propanol, isopropanol, and the like. The kneading and granulating operations carried out by adding such auxiliary agents for making the preparation and by adding such a solvent may be conducted using the conventionally used apparatus. For example, a fluidized bed granulator, a tumbling granulator, an extrusion granulator or a spray-drying drier may be used. The solid compositions may also be prepared via freeze drying.

Powders can be prepared by compounding the ingredients and optionally calcium carbonate, and, if necessary, further orally acceptable additive(s), and mixing in a conventional manner.

The powdered compositions of the present disclosure may be made by including pulverizing (and, optionally, screen filtering) particulate material to have independent particle sizes from about 0.1 to about 1 mm, about 1 to about 500 microns, about 1 to about 250 microns, about 1 to about 150 microns, about 5 to about 100 microns, about 6 to about 35 microns, about 6 to about 13 microns in average diameter of individual particles. In one embodiment, the orally acceptable particulate is pulverized so that, in a bed having a volume of at least 125 cubic millimeters, at least 99 percent of individual particles in the bed have an independent calcium carbonate particle size from about 1 to about 150 microns.

Granules can be prepared by any one of known methods for preparing granules such as dry granulation, layering granulation, impregnated-granulation, etc.

For dry granulation, a mixture of ingredients with optional additive(s) is subjected to granulation with a roller compactor, a roll granulator, etc.

For layering granulation, a mixture similar to the above is added to a rolling inactive carriers while spraying a binder solution with a centrifugal fluidized bed granulator or the like to make the mixture adhere to the carries. Examples of the inactive carrier that used in this method include crystals of sugars or inorganic salts such as crystalline lactose, crystalline cellulose, crystalline sodium chloride, etc., and spherical granules such as spherical granules of crystalline cellulose (brand name: Avicel SP, Asahi Kasei Corporation), spherical granules of crystalline cellulose and lactose (brand name: Nonpareil-NP-5 and NP-7, Freund Co., Ltd.), spherical granules of purified white sugar (brand name: Nonpareil-103, Freund Co., Ltd.), spherical granules of lactose and a starch, etc.

For impregnating granulation, a solution containing potassium peroxymonosulfate and other ingredients at an appropriate concentration is mixed with porous carriers thereby a sufficient amount of solution is made to retain in the cavities of the carrier, which is followed by drying to remove the solvent. Examples of the porous carrier that can be used include magnesium aluminometasilicate (brand name: Neusiline, Fuji Chemical Industry Co., Ltd.), calcium silicate (Florite, Eisai Co., Ltd.), etc. Examples of the solvent include ethanol, methanol, or the like.

In another aspect, the present disclosure provides a method of bleaching the teeth to remove or diminish tenacious stains, comprising mixing the solid oral care composition described herein (e.g., Composition 1 or any of 1.1-26) into water, a mouthrinse base, or a toothpaste base, optionally until the composition dissolves, followed by applying the composition to the teeth. The composition can be applied to the teeth as a solution or a suspension. As a solution, e.g., a mouthwash, the composition may be used as a rinse. As a suspension, e.g., a paste, the composition can be applied to the teeth with a toothbrush or similar device.

In another aspect, the present disclosure provides the use of a solid oral care composition as described herein (e.g., Composition 1 or any of 1.1-26) for the removal or diminution of a tenacious tooth stain, e.g., tobacco and/or coffee stains. Such use may comprise mixing of the solid oral care composition into water, a mouthrinse base, or a toothpaste base, optionally until the composition dissolves or is homogenized, followed by applying the composition to the teeth. The composition can be applied to the teeth as a solution, a suspension, or a paste. As a solution, e.g., a mouthwash, the composition may be used as a rinse. As a suspension, e.g., a paste, the composition can be applied to the teeth with a toothbrush or similar device.

The term "mouthwash" or "mouthrinse" generally denotes liquid formulations which are used to rinse the surfaces of the oral cavity and provide the user with a sensation of oral cleanliness and refreshment. The mouthrinse is an oral composition that is not intentionally swallowed for purposes of systemic administration of therapeutic agents, but is applied to the oral cavity, used to treat the oral cavity and then expectorated. A mouthrinse composition will usually contain an aqueous continuous phase.

A typical mouthrinse composition consists of a liquid carrier such as water, a humectant, such as glycerin, sorbitol, propylene glycol a surfactant, such as a Pluronics, sodium lauryl sulfate, a sweetening agent, such as sodium saccharin, xylitol a flavoring agent, a coloring agent, and a preservative agent, such as potassium sorbate, sodium benzoate. The composition may also include buffering agents that have the capability to buffer to a final pH of 6.5-8, such as sodium phosphates, an anti-cavity agent, such as sodium fluoride, and an anti-bacterial agent such as cetyl pyridinium chloride.

Provided is a solid oral care composition (Composition 1) for the removal or diminution of tenacious tooth stains (e.g., tobacco and/or coffee stains), comprising a tooth whitening effective amount of an alkali metal salt of peroxymonosulfate.

1.1. Composition 1, wherein the salt of peroxymonosulfate is sodium peroxymonosulfate, potassium peroxymonosulfate, or lithium peroxymonosulfate, or a combination thereof;

1.2. Composition 1 or 1.1, wherein the salt of peroxymonosulfate is potassium peroxymonosulfate;

1.3. Composition 1.2, wherein the potassium peroxymonosulfate is a triple salt of potassium peroxymonosulfate, potassium hydrogen sulfate and potassium sulfate, optionally wherein the triple salt comprises about 47%-50% by weight of potassium peroxymonosulfate, e.g., 47% or 50% by weight of potassium peroxymonosulfate;

1.4. Any of the preceding compositions, wherein the composition comprises an effective amount of peroxymonosulfate salt which is 0.1% to 50%, by weight of the composition, e.g., 0.75% to 40%, or 1% to 20%, or 1% to 10%, or 0.5% to 10%, or 1 to 10%, or 2 to 8%, or 4 to 6% or about 5%, by weight of the composition;

1.5. Any of the preceding compositions, further comprising an abrasive, optionally, wherein the abrasive is present in an amount of 10-95% by weight of the composition, e.g., 30-95%, or 50-95%, or 60-95%, or 70-95%, or 80-95% or 85-95%, or 85-90% or about 86%;

1.6. Composition 1.5, wherein the abrasive is selected from calcium carbonate (precipitated or natural), sodium carbonate, sodium chloride, sodium bicarbonate, silica, arginine bicarbonate, calcium phosphate, calcium pyrophosphate, dicalcium phosphate, zinc oxide, calcined alumina, or combinations thereof;

1.7. Composition 1.5 or 1.6, wherein the abrasive is natural calcium carbonate, precipitated calcium carbonate, or a mixture thereof;

1.8. Any of the preceding composition, further comprising a drying agent;

1.9. Composition 1.8, wherein the drying agent is selected from calcium lactate, calcium lactophosphate, double salts of calcium lactate, phosphates, pyrophosphates, polyphosphates, orthophosphates, metaphosphates, silica, alumina, bicarbonates, polymetaphosphates, aluminum silicate, zirconium silicates, bentonite, and combinations thereof;

1.10. Any of the preceding compositions, wherein the drying agent comprises a pyrophosphate, alumina, sodium bicarbonate, or combinations thereof;

1.11. Any of the preceding compositions, wherein the drying agent comprises an alkali metal salt of pyrophosphate, e.g., tetrasodium pyrophosphate or tetrapotassium pyrophosphate;

1.12. Any of the preceding compositions, wherein the composition is in the form of a tablet, powder or granule and is packaged in a moisture free environment;

1.13. Any of the preceding compositions, wherein the composition is packaged in a single-use container comprising a tin can, tube, or sachet;

1.14. Any of the preceding compositions, wherein the composition contains no water or water in an amount of less than 4%, or less than 3%, or less than 2%, or less than 1%, or less than 0.5%, or about 0.0001% to about 4%, or about 0.0001% to about 0.5% or about 0.0001% to about 0.1%, or about 0.001% to 4%, by weight;

1.15. Any of the preceding compositions, wherein the drying agent is present in an amount of about 0.1% to about 60%, about 1% to about 30%, about 1% to about 10%, or about 1% to about 5%, or about 2%, or about 3%, or about 4% or about 5%, by weight of the total composition;

1.16. Any of the preceding compositions, comprising a disintegrating agent is selected from natural starches, such as maize starch, potato starch; directly compressible starches such as starch 1500; modified starches such as carboxymethyl starches and sodium starch glycolate; starch derivatives such as amylose; cross-linked polyvinylpyrrolidones, such as crospovidones; modified celluloses such as cross-linked sodium carboxymethylcelluloses; alginic acid; sodium alginate; microcrystalline cellulose; methacrylic acid-divinylbenzene copolymer salts; light silicic anhydride; calcium silicate; magnesium metasilicate aluminate; carboxymethyl cellulose; and mixtures thereof;

1.17. Any of the preceding compositions, comprising a binder wherein the binder is selected from starches, natural gums, (e.g., xanthan gum), cellulose gums, microcrystalline cellulose, maltodextrins, methyl cellulose, cellulose ethers, sodium carboxymethylcellulose, ethylcellulose, gelatin, polyethylene glycol, polyvinylpyrrolidone, pectins, alginates, polyacrylamides, polyvinyloxazolidone, polyvinyl alcohols and mixtures thereof;

1.18. Composition 1.17, wherein the binder is present in the composition in an amount of from 10% by weight to about 60% by weight, or from about 15% by weight to about 50% by weight, or from about 25% by weight to about 40% by weight;

1.19. Any of the preceding compositions, further comprising a buffering agent selected from an anhydrous carbonate such as sodium carbonate, a sesquicarbonate, a bicarbonate such as sodium bicarbonate, a silicate, a bisulfate, a citrate, a phosphate such as monopotassium phosphate and dipotassium phosphate, or a combination thereof in an amount of about 5.0% to about 35%, or about 10% to about 30%, or about 15% to about 25%, by weight of the total composition;

1.20. Any of the preceding compositions, wherein the composition is effervescent and contains an effervescent acid and an effervescent base;

1.21. Composition 1.20, wherein the effervescent acid is citric acid, ascorbic acid, malic acid, adipic acid, tartaric acid, fumaric acid, succinic acid, sodium acid pyrophosphate, lactic acid, hexamic acid, citraconic anhydride, glucono-D-lactone, succinic anhydride, potassium bitartrate, acid citrate salts, sodium dihydrogen phosphate, disodium dihydrogen phosphate, sodium acid sulfite, and combinations thereof, and is present in the composition in an amount of from 10% by weight to about 60% by weight, from about 15% by weight to about 50% by weight, or even from about 25% by weight to about 40% by weight;

1.22. Composition 1.20 or 1.21, wherein the effervescent base is sodium bicarbonate, sodium carbonate, sodium sesquicarbonate, potassium carbonate, potassium bicarbonate, calcium carbonate, magnesium carbonate, magnesium oxide, sodium glycine carbonate, L-lysine carbonate, arginine carbonate, zinc carbonate, zinc oxide and mixtures thereof, and is present in the composition in an amount of from 10% by weight to about 60% by weight, or from about 15% by weight to about 50% by weight, or from about 25% by weight to about 40% by weight;

1.23. Any of the preceding compositions, further comprising a lubricant in an amount from about 1% by weight to about 15% by weight, or from about 1% by weight to about 12% by weight, or from about 2% by weight to about 10% by weight, or from about 3% by weight to about 8% by weight;

1.24. Any of the preceding compositions, containing an additional whitening agent;

1.25. Any of the preceding compositions, additionally comprising one or more flavor agents, one or more fillers, one or more surfactants, one or more color agents, or any combination of two or more thereof.

1.26. Any of the preceding compositions which is a toothpowder.

EXAMPLES

Exemplary embodiments of the present disclosure will be illustrated by reference to the following examples, which are included to exemplify, but not to limit the scope of the present invention.

In the examples and elsewhere in the description of the invention, chemical symbols and terminology have their usual and customary meanings. Temperatures are in degrees Celsius unless otherwise indicated. The amounts of the components are in weight percent based on the standard described; if no other standard is described then the total weight of the composition is to be inferred. Various names of chemical components include those listed in the CTFA International Cosmetic Ingredient Dictionary (Cosmetics, Toiletry and Fragrance Association, Inc., 7$^{th}$ ed. 1997).

Example 1: Bleaching of Tobacco Actives

Loose leaf tobacco is soaked in water for 24 hours then filtered to yield a yellow-brown solution, which is diluted with 0.1M phosphate buffer (pH 7.5) until the absorbance at 405 nm is between 0.75 and 1.0 on a Perkin-Elmer Envision Multi-Plate Reader. 5 mL of this tobacco solution is added to a set of scintillation vials. A bleaching agent is added to each vial: Caroat to 5% w/v (about 2.5% w/v KHSO5), Caroat to 10% w/v (about 5% w/v KHSO5), or hydrogen peroxide (HP) to 5% w/v (using a 35% w/v hydrogen peroxide solution). The Absorbance of each solution is measured at 405 nm over the course of 30 minutes. A reduction in absorbance indicates bleaching of the colored tobacco actives.

TABLE 1

| Time | 0 min | 5 min | 9 min | 13 min | 19 min | 27 min | 30 min |
|---|---|---|---|---|---|---|---|
| 5% MPS | 0.86 | 0.44 | 0.34 | 0.33 | 0.24 | 0.19 | 0.17 |
| 2.5% MPS | 0.86 | 0.41 | 0.34 | 0.31 | 0.26 | 0.24 | 0.23 |
| 5% HP | 0.80 | 0.75 | 0.74 | 0.73 | 0.72 | 0.71 | 0.70 |

The results demonstrate that both 2.5% w/v MPS and 5% w/v MPS are superior to 5% hydrogen peroxide in the bleaching of the active agents from tobacco leaf which stain the teeth.

Example 2: MPS is Significantly More Effective than Hydrogen Peroxide in Removing Tobacco Stains from Bovine Incisors Bovine incisors are mounted individually in resin blocks and stained with a tobacco solution. The incisors are then brushed with an abrasive paste until the initial L values are between 60 and 65 (see below). The mounted incisors are then placed in a tray and inserted into an automated brushing machine in which the incisors will be brushed using a commercial toothbrush head. Teeth are brushed for two minutes at 120 strokes per minute under a pressure of 0.25 kg. A slurry composed of 1:1 by weight of test dentifrice to artificial saliva is used for brushing. After brushing is complete, residual dentifrice is washed off with distilled water, the teeth are gently blotted dry and then spectrophotographic measurements are taken. The cycle is repeated 14 times.

Change in whiteness is calculated using the parameter $W^*$, which is a measure of whiteness calculated as: $W^* = ((a^*-0)^2+(b^*-0)^2+(L^*-100)^2)^{1/2}$. Change in whiteness, $\Delta W^*$, is then calculated as: $\Delta W^* = W^* \text{treatment} - W^* \text{baseline}$. An increase in the $\Delta W^*$ value indicates a progressive whitening of the teeth, and therefore, a bleaching of the tenacious tobacco stains.

An MPS-based toothpowder dentifrice according to the present invention is compared to a matching placebo containing no MPS. The results are shown in Table 2 below. The experiment shows that the MPS-based dentifrice results in significantly better bleaching of the tobacco stains on bovine tooth enamel compared to the MPS-free placebo. The composition of the MPS-based toothpowder is shown in Table 4 below.

TABLE 2

| In-vitro Brushing (MPS v. Placebo) | | | | | | | |
|---|---|---|---|---|---|---|---|
| Treatment | 0 | 2 | 4 | 6 | 8 | 10 | 12 | 14 |
| 5% MPS | 0.00 | 2.62 | 3.81 | 3.81 | 5.20 | 6.88 | 7.11 | 8.23 |
| Placebo | 0.00 | 0.92 | 1.21 | 2.06 | 2.59 | 2.84 | 3.23 | 3.70 |

In addition, the 5% MPS-based toothpowder is also compared to a 2% hydrogen peroxide dentifrice side-by-side (as in the procedure described above). The results are shown in Table 3 below. The experiment shows that the MPS-based toothpowder produces significantly better bleaching of the tobacco stains on bovine tooth enamel compared to the hydrogen peroxide based dentifrice.

TABLE 3

In-vitro Brushing (MPS v. Hydrogen Peroxide)

| Treatment | 0 | 2 | 3 | 4 | 6 | 8 | 9 | 10 | 12 | 14 |
|---|---|---|---|---|---|---|---|---|---|---|
| 5% MPS | 0.00 | 2.62 | | 3.81 | 3.81 | 5.20 | | 6.88 | 7.11 | 8.23 |
| 2% HP | 0.00 | | 0.74 | | 1.43 | | 2.30 | | 3.20 | 3.01 |

The compositions of the MPS-based toothpowder and its matching placebo are shown in Table 4 below.

TABLE 4

MPS-Whitening Powder and Matching Placebo (% w/w)

| | Whitening | Placebo |
|---|---|---|
| Calcium carbonate | 85.64% | 95.64% |
| Potassium MPS Triple Salt* | 10.00% | 0.00% |
| Sodium monofluorophosphate | 0.76% | 0.76% |
| Sodium saccharin | 0.60% | 0.60% |
| Sodium lauryl sulfate | 3.00% | 3.00% |
| Total | 100% | 100% |

*Triple Salt is 47 wt % KHSO$_5$

The composition of the 2% hydrogen peroxide dentifrice is shown in Table 5 below. The cross-linked polyvinylpyrrolidone-hydrogen peroxide complex used is approximately 18% hydrogen peroxide by weight.

TABLE 5

HP Dentifrice (% w/w)

| | Whitening |
|---|---|
| Humectants | 52.7% |
| Polymers | 11.75% |
| Anticalculus agents | 1.90% |
| Sodium monofluorophosphate | 0.76% |
| Silica | 1.75% |
| Calcium Pyrophosphate | 15.00% |
| Flavors, Color, Preservative | 3.14% |
| Sodium lauryl sulfate | 2.00% |
| Hydrogen Peroxide-cPVP complex | 11.00% |
| Total | 100% |

The invention has been described above with reference to illustrative Examples, but it is to be understood that the invention is not limited to the disclosed embodiments. Alterations and modifications that would occur to one of skill in the art upon reading the specification are also within the scope of the invention, which is defined in the appended claims.

What is claimed is:

1. A solid oral care composition for the removal or diminution of tenacious tooth stains, wherein the tenacious stains are tobacco stains, comprising a tooth whitening effective amount of an alkali metal salt of peroxymonosulfate and 70 to 95% by weight of an abrasive, wherein the salt of peroxymonosulfate is potassium peroxymonosulfate and wherein the tooth whitening effective amount of the peroxymonosulfate salt is 2% to 8%, by weight of the composition, and wherein the composition does not comprise any other peroxide compound whitening agent in addition to the peroxymonosulfate salt, and wherein the composition is a toothpowder.

2. The composition of claim 1, wherein the potassium peroxymonosulfate is a triple salt of potassium peroxymonosulfate, potassium hydrogen sulfate and potassium sulfate, optionally wherein the triple salt comprises about 47%-50% by weight of potassium peroxymonosulfate.

3. The composition of claim 1, wherein the composition comprises an effective amount of peroxymonosulfate salt which is 2% to 4% by weight of the composition.

4. The composition of claim 1, wherein the effective amount of peroxymonosulfate salt is about 5% by weight of the composition.

5. The composition of claim 1, wherein the abrasive is selected from calcium carbonate, sodium carbonate, sodium chloride, sodium bicarbonate, silica, arginine bicarbonate, calcium phosphate, calcium pyrophosphate, dicalcium phosphate, zinc oxide, calcined alumina, and combinations thereof.

6. The composition of claim 5, wherein the abrasive is calcium carbonate.

7. A method of bleaching the teeth to remove or diminish tenacious stains, wherein the tenacious stains are tobacco stains, comprising the steps of (1) mixing a solid oral care composition, which composition is a toothpowder and which comprises a tooth whitening effective amount of an alkali metal salt of peroxymonosulfate and 70 to 95% of an abrasive by weight of the toothpowder composition, into (a) water to form a solution or suspension, (b) a mouthrinse base to form a solution or suspension, or (c) a toothpaste base to form a suspension or paste, followed by (2) applying the resulting solution, suspension, or paste to the teeth;

wherein the salt of peroxymonosulfate is potassium peroxymonosulfate and wherein the tooth whitening effective amount of the peroxymonosulfate salt is 2% to 8%, by weight of the toothpowder composition, and wherein the toothpowder composition does not comprise any other peroxide compound whitening agent in addition to the peroxymonosulfate salt.

8. The method according to claim 7, wherein the toothpowder composition comprises an effective amount of peroxymonosulfate salt which is 2% to 4% by weight of the toothpowder composition.

9. The method according to claim 7, wherein the toothpowder composition comprises an effective amount of peroxymonosulfate salt which is about 5% by weight of the toothpowder composition.

10. The method according to claim 7, wherein the abrasive comprises calcium carbonate.

11. The method according to claim 7, wherein the peroxymonosulfate salt is potassium peroxymonosulfate in an amount of 2% to 4% by weight of the toothpowder composition, and wherein the abrasive comprises calcium carbonate.

12. The method according to claim 7, wherein the toothpowder composition consists of the potassium peroxymonosulfate, the abrasive, and optionally one or more of drying agents, lubricants, disintegrating agents, buffering agents, binders, flavor agents, fluoride sources, surfactants, preservatives, and color agents.

13. The method according to claim 7, wherein the toothpowder composition consists of the potassium peroxymonosulfate, the abrasive, a fluoride source, and a surfactant.

14. The method according to claim 7, wherein the toothpowder composition consists of 2 to 8% potassium peroxymonosulfate, and 70-95% calcium carbonate abrasive, each by weight of the toothpowder composition, and optionally a fluoride source, a surfactant, or both.

15. The method according to claim 7, wherein the toothpowder composition is mixed with the water or mouthrinse base, until the toothpowder composition dissolves, and the resulting solution is applied to the teeth.

16. The method according to claim 7, wherein the toothpowder composition is mixed with the water or mouthrinse base to form a suspension, and the resulting suspension is applied to the teeth.

17. The method according to claim 7, wherein the toothpowder composition is mixed with a toothpaste base to form a suspension or paste, and the resulting suspension or paste is applied to the teeth.

\* \* \* \* \*